US009072612B2

(12) United States Patent
Sethi et al.

(10) Patent No.: US 9,072,612 B2
(45) Date of Patent: Jul. 7, 2015

(54) JAW THRUST APPLIANCE

(76) Inventors: Manu Sethi, Canfield, OH (US);
Sangeetha Sethi, Canfield, OH (US)

(*) Notice: Subject to any disclaimer, the term of this patent is extended or adjusted under 35 U.S.C. 154(b) by 275 days.

(21) Appl. No.: 13/349,003

(22) Filed: Jan. 12, 2012

(65) Prior Publication Data

US 2012/0186591 A1 Jul. 26, 2012

Related U.S. Application Data

(60) Provisional application No. 61/434,958, filed on Jan. 21, 2011.

(51) Int. Cl.
*A61F 5/56* (2006.01)
*A63B 23/03* (2006.01)
*A61H 1/02* (2006.01)

(52) U.S. Cl.
CPC .............. *A61F 5/56* (2013.01); *A63B 23/032* (2013.01); *A61H 1/0218* (2013.01); *A61F 5/566* (2013.01)

(58) Field of Classification Search
CPC .................................................. A61H 1/0218
USPC ........ 128/848, 846.859, DIG. 23, 845; 433/5, 433/73, 229; 482/11; 602/32
See application file for complete search history.

(56) References Cited

U.S. PATENT DOCUMENTS

| 4,597,738 | A | | 7/1986 | Sander |
| 4,782,824 | A | | 11/1988 | Davies |
| 5,524,639 | A | * | 6/1996 | Lanier et al. ................ 5/630 |
| 5,682,632 | A | | 11/1997 | Cotroneo |
| 7,121,824 | B2 | | 10/2006 | Keles |
| 7,951,102 | B2 | | 5/2011 | Gefen |
| 8,191,553 | B2 | * | 6/2012 | Haworth et al. ............. 128/845 |
| 2008/0173313 | A1 | * | 7/2008 | Brady et al. ................ 128/848 |
| 2011/0308528 | A1 | * | 12/2011 | Ciardullo .................... 128/848 |

* cited by examiner

*Primary Examiner* — Alireza Nia
*Assistant Examiner* — Tarla Patel
(74) *Attorney, Agent, or Firm* — Daniel Boudwin; Global Intellectual Property Agency LLC

(57) ABSTRACT

An extra-oral medical device is disclosed for treating respiratory conditions and maintaining an open airway. The device comprises a pair of jaw thrusters that affix to a headgear appliance encircling or otherwise attaching around a user's head. The thrusters include a pair of pads that attach to the headgear via two adjustable ear surrounds and place a forward load against the angle of a user's mandible. The forward load forces the mandible and the tongue forward, displacing the tongue from the posterior oropharynx and performing a jaw thrust maneuver for airway management. The device is adapted for medical and personal use, wherein the headgear can be worn while sleeping to treat sleep apnea, excessive snoring and other respiratory disorders, or alternatively may be used by medical professionals to maintain an open airway during a procedure or medical emergency.

13 Claims, 3 Drawing Sheets

JAW THRUST APPLIANCE

CROSS REFERENCE TO RELATED APPLICATION

This application claims the benefit of U.S. Provisional Application No. 61/434,958 filed on Jan. 21, 2011, entitled "Jaw Thrust Appliance (JTA)."

BACKGROUND OF THE INVENTION

1. Field of the Invention

The present invention relates to jaw and throat devices for the purposes of maintaining an airway for medical procedures or for treating sleeping and breathing disorders. More specifically, the present device is an extra-oral headgear that performs a jaw thrust maneuver by forcing the mandible forward via a pair of thrust pads connected to a head-worn band and a plurality of supports that surround a user's ears.

The jaw thrust maneuver is a medical airway management practice in which the mandible (jaw) of a user is pushed forward to maintain an opening between the external environment and the user's lungs. Forcing the mandible forward pushes the tongue forward and prevents it from occluding the entrance of the trachea by falling back into the pharyngeal air passage. Several circumstances and situations may require such a maneuver, including treatment of those individuals with sleeping or respiratory disorders, those undergoing a medical procedure and in a pharmacologically induced unconsciousness, and those in a medical emergency wherein the user is unconscious and in a supine position. Relaxation of the muscles of the pharynx, mandible and neck cause a collapsing inward and narrowing of the air passage from the mouth to the lungs, restricting the user's air supply and causing a potentially life threatening loss of oxygen (asphyxiation).

The present invention is a new and novel means of performing a jaw thrust maneuver on a patient or user, wherein a pair of thrust pads worn around ear supports that attach to an extra-oral headgear provide a means to comfortably and conveniently displace the jaw forward. The thrust pads place load on the angle of the mandible from the outside of a user's head, while the forward position of the jaw is supported by the ear supports that connect to the headgear encircling or otherwise attaching to the user's head. The present device is adapted to be utilized in several circumstances, including treatment of sleeping and breathing conditions, to emergency and critical care. The device can be deployed by a medical professional or be utilized by an individual in the comfort of his or her home for personal use. The following is a contemplated list of such treatments and scenarios in which the present device may function:

Sleeping disorders: for users with sleeping and respiratory disorders, including excessive snoring and sleep apnea, obstruction of the user's airway caused by the relaxation of the mouth and throat muscles can cause a significant decrease in blood oxygen levels (hypoxemia), as well as sleep deprivation induced by the interrupted sleep and reduced REM sleep for the user. These conditions can lead to serious health risks and complications, while at the same time affecting a user's partner via the audible nature of excessive snoring, which can disturb sleeping patterns and cause daytime drowsiness for both individuals as a result of a lack of adequate sleep. The present invention is intended to treat users having such disorders, including those that snore and/or have a history of diagnosed or undiagnosed sleep apnea. These conditions are a growing public health concern, as studies have shown that nearly 30% of our population is obese, which is a major risk factor and cause of obstructive sleep apnea, along with age and aggravating factors such as smoking and diabetes. The present invention is provided to control the mandible of a user and prevent airway restrictions, while providing this control via a non-obtrusive and relatively convenient headgear device that does not otherwise affect a user's posture or comfort.

Medical procedures and anesthesia: obstructions of a patient's airway is possible during medical procedures wherein a user is asleep, either naturally or pharmacologically-induced. A supine user under sedation or while in a coma can suffer similar airway restrictions caused by the relaxation of the mouth and tongue muscles, which can lead to an occlusion of the airway and a reduction in oxygen levels. Under sedation-type anesthesia, an anesthesiologist or assistant must be vigilant and actively maintain a patient's airway during a procedure. This can be accomplished through several different maneuvers, each one requiring the physician's hand or hands to be actively utilized, which can otherwise be utilized for patient monitoring or treatment. This limits the physician's ability to properly and fully manage the patient care while under anesthesia, particularly if a serious problem or complication arises during the procedure of which the physician is required to address and fix. A more efficient means of maintaining an airway is required, and one that does not require constant monitoring by a doctor, nurse or health professional. The present invention provides such a device, and one that does not overly engage and interfere with the user's mouth or head.

Urgent and emergency care: first responders and physicians treating patients with traumatic injuries encounter similar issues as those treating a sedated patient, wherein a patient's airway may be compromised while unconscious or while being treated in a supine position. In emergency situations, airway restriction is a concern. Larger neck braces and head gear are generally utilized to stabilize the patient's airway and neck; however it may be desired to carry and utilize a smaller device that can accomplish a jaw thrust maneuver for emergency treatment and prior to cardiopulmonary resuscitation activities. The present invention can be transported and deployed in a number of environments with little to no storage requirements, wherein its use facilitates an open airway and improved airway maintenance to prevent asphyxiation.

While snoring is a very common problem in the general population, of greater concern is the incidence of obstructive sleep apnea, which is increasing dramatically as our population grows older and becomes more obese. Apnea is defined as the cessation of oronasal airflow for at least 10 seconds or more. If this occurs 30 or more times in a 7 hour sleep interval, it is defined as obstructive sleep apnea. Most, if not all patients with undiagnosed sleep apnea are not aware that they have it. In fact, it has been shown that up to 70% of patients presenting for medical procedures or surgery may have undiagnosed obstructive sleep apnea (OSA). People with OSA can have daytime hypersomnolence, including easily falling asleep in un-stimulating environments (e.g. watching TV or driving). They can also have irritability, personality changes, headaches and/or depression. If left untreated, OSA can contribute to systemic hypertension, pulmonary hypertension, and heart failure leading to cor pulmonale, cardiac arrhythmias and congestive heart failure. These individuals are also at a higher risk for perioperative complications such as hypoxemia (low oxygen levels), need for re-intubation, hypertension, dysrhythmias and unplanned hospital admission.

Those who snore and/or who have obstructive sleep apnea (OSA) have problems related with the soft tissue surrounding their airway, as well as their tongue collapsing into the posterior portion of their oropharynx. This restricts air movement and creates turbulent airflow that causes the sounds of snoring. When this collapse is severe (i.e. in OSA), complete airway closure occurs, preventing air flow and leading to dangerously low oxygen levels in the body. A significant contributing factor to airway collapse is the previously mentioned posterior movement of the tongue into the posterior oropharynx. Therefore, in the vast majority of individuals, anterior displacement of the tongue is usually all that is needed to help relieve airway obstruction and therefore maintain airway patency. The present invention provides a device for remedying this common condition.

2. Description of the Prior Art

The present invention is related to an external appliance that provides a jaw thrust maneuver for patients suffering from certain conditions or in need of medical attention. Present devices utilized to treat such conditions, most specifically sleep apnea, including larger devices and breathing apparatuses to maintain active breathing during the night. Those patients in intensive care and those with extreme cases of sleep apnea may utilize ventilators to maintain an open airway and to maintain breathing. One category of breathing masks includes CPAP or BiPAP masks that patients with sleep apnea wear at night. These devices maintain airway patency by forcing positive air pressure down a patient's airway. The major drawback associated with these devices is that they are uncomfortable to wear. Some patients complain that they are suffocating and they restrict the patient's body position while sleeping to a supine position. Other drawbacks are that these devices are expensive and can be noisy, disturbing normal sleep patterns and limiting a patient's willingness to utilize the device as a means to treat severe sleep apnea. Due to these problems, and the fact that patients have to undergo sleep studies and referrals from their family physicians to obtain such devices, many patients are noncompliant with using their CPAP or BiPAP machine.

Another category of devices utilized in the treatment of sleep apnea involves intra-oral mandibular advancement devices. These devices move the jaw forward by intra-orally displacing the mandibular teeth forward (thereby creating an under bite). Even though this type of device solves some of the problems with the CPAP/BiPAP ventilator devices and aids in the treatment of sleep apnea (i.e. less expensive, not suffocating or noisy and doesn't require sleep studies or physician referrals), these device still have limitations. An intraoral device is an intrusive external element within the mouth that some individual may not tolerate sleeping. These devices can stimulate the gag reflex, making a person nauseated or vomit, and further are best utilized by an individual keeping his or her mouth closed and teeth clenched on/in the device for proper position thereof. This type of device is not helpful for mouth breathers, and is found to generate high rates of non-compliance.

The present invention eliminates the suffocating action of intra-oral devices and the expense of CPAP or BiPAP machines, while being flexible to be utilized individually by a user or in medical treatment of patients and administered by trained professionals. The device allows a user to sleep in any position (supine, lateral or prone) and alleviates common drawbacks of devices utilized in the treatment of sleeping disorders and airway management for medical procedures and emergencies.

Several devices have been patented and disclosed in the prior art that relate to airway management and devices that perform a jaw thrust maneuver on a patient. These devices have familiar design elements for the purposes of thrusting a jaw forward via the mandible angle; however the structure and spirit of the disclosed devices differ drastically from the present disclosure. Most devices in the art are bulky or intrusive for the user, and further not conducive for treating airway restrictions while allowing the user to sleep in any desired position. The present invention is ideally suited for either personal use, wherein normal sleeping positions and posture is not affected, or alternatively for medical procedure and patient care purposes wherein an airway must be actively monitored and protected from occlusion. The following devices are considered the most relevant devices in the prior art to the present disclosure.

U.S. Pat. No. 5,682,632 to Cotroneo is one such device that discloses a jaw thrust support device in the form of a contoured mold or cushion. The device engages the angles of the mandible to accomplish a jaw thrust maneuver to open a patient's airway while in a prone position. The mold conforms to the patient and angles his or her head and neck while supporting the jaw and forcing it forward. The forward position of the jaw clear an airway by lifting the tongue from the patient's oropharynx and hypopharynx and lifting the epiglottis from in front of the patient's laryngeal opening. The Cotroneo device is a molded contour that the user lays against. The shape of the contour provides the jaw thrust maneuver, as opposed to a headgear device. While providing a novel means to open an otherwise redistricted airway, the Cotroneo device is best suited for use with unconscious patients or those being medically treaded. The present invention provides a device that can be utilized in a number of circumstances for the purposes of clearing user's airway, including for treatment of sleep apnea, excessive snoring or for ensuring an open airway while under anesthesia.

U.S. Pat. No. 4,782,824 to Davies is another device that describes a neck-worn device that maintains and open airway passage, comprising a lower portion arranged to rest on the upper thorax and an upper portion having a means to lifting and thrusting forward the lower jaw. The posterior portion of the device prevents backward movement of the patient's jaw, positioning the jaw in such a way to prevent airway restrictions caused by the tongue falling into the airway or the pharynx closing because of the positioning of the jaw and throat. The Davies device is neck-worn, and provides a means to perform a jaw thrust maneuver on an unconscious or surgical patient undergoing anesthesia. It is not well adapted for everyday use to correct sleep disorders and to be voluntarily worn by a user while asleep.

U.S. Pat. No. 4,597,738 to Sander describes an orthodontic device that is adapted to thrust a lower jaw forward using internal thrust plate structures within the interior of a user's mouth. An upper and lower jaw thrust plate are provided, which connect to the front teeth region with activating rods and slideways, respectively, creating a displacement of the lower jaw with respect to the upper for treatment of supraocclusion or subocclusion, in which the lower jaw is excessively set back from the upper jaw. The Sander device is an orthodontic device adapted to be secured within a user's mouth to correct jaw alignment issues. It is not provided to maintain an airway or to treat breathing and sleep disorders, as provided by the present jaw thrust device of the present invention. The present invention is adapted to conform to the exterior of a user's head and operate to force the mandible forward to prevent airway restrictions while sleeping or undergoing anesthesia.

The structure and spirit of the forgoing prior art patents differ significantly from the present invention. These devices provide novel means for performing a jaw thrust maneuver, but fail to disclose a device that can be actively worn by a conscious patient to correct sleep disorders, while simultaneously offering the ability to be utilized in surgical procedures with an unconscious individual under anesthesia. The aforementioned devices are considered relevant to the present disclosure, but lack the flexibility, comfort and convenience offered by the present device, which is exteriorly mounted and secured to a user's head to maintain a sufficient airway to treat sleeping and breathing disorders, and further to maintain an open airway during medical procedures.

U.S. Pat. No. 7,951,102 to Gefen describes a cervical collar that maintains an airway of a trauma patient by immobilizing the patient's head and neck. The collar comprises a restricting frame and a jaw clasp to control the jaw of a patient and connect the jaw clasp to the restricting frame to prevent movement of the patient's head, neck and jaw. The jaw clasp performs a jaw thrust maneuver to maintain an open airway, while the clasp positioning is controlled by a plurality of movable mover elements to ensure secure fitment and restraint. The Gefen device is well suited for trauma patients and those being transported while requiring an open airway, but is less suited for individual use under normal circumstances. The present invention provides a means to thrust a patient's jaw forward and control an airway that offers minimal interference with the user's body. While providing a means to thrust a jaw forward, the Gefen device is a more intrusive device that fulfills a different need in the art than that of the present invention, which is minimally intrusive to a user's head and neck.

Finally, U.S. Pat. No. 7,121,824 to Keles describes a face-bow headgear device to correct anterior open bites. The device is an extra-oral headgear that creates a frame on the user's face to correct oral conditions related to offset bites. The device is a head gear that operates with the jaw, but does not provide a means to thrust the mandible forward for the purposes of a jaw thrust maneuver or for correcting various sleep and breathing disorders. While providing a novel headgear that attends to oral alignment disorders, the Keles device fails to disclose a headgear that fulfills the same goals and needs of the present invention, which is an external, extra-oral device that forces the mandible forward to reduce restrictions on the pharynx and prevent the tongue from closing an airway while sleeping or while sedated.

It is therefore submitted that the present invention is substantially divergent in design elements from the prior art, and consequently it is clear that there is a need in the art for an improvement to existing extra-oral jaw thrust appliances. In this regard the instant invention substantially fulfills these needs.

SUMMARY OF THE INVENTION

In view of the foregoing disadvantages inherent in the known types of extra-oral jaw thrust appliances now present in the prior art, the present invention provides a new jaw thrust appliance wherein the same can be utilized for providing convenience for the user while treating sleeping and breathing disorders or for maintenance of a patient's airway by a medical professional.

It is therefore an object of the present invention to provide a new and improved extra-oral jaw thrust appliance device that has all of the advantages of the prior art and none of the disadvantages.

Another object of the present invention to provide an extra-oral jaw thrust appliance that performs a jaw thrust maneuver on a user by displacing the angle of the mandible and forcing the jaw and tongue forward to maintain an open airway, preventing the tongue from falling into the posterior oropharynx to prevent asphyxiation.

A further object of the present invention to provide an extra-oral jaw thrust appliance that may be utilized by a user to treat sleeping and breathing disorders, and one that can be personally administered.

Yet another object of the present invention to provide an extra-oral jaw thrust appliance that can be utilized for airway management by medical professionals during a medical procedure or emergency.

A final object of the present invention to provide an extra-oral jaw thrust appliance that is comfortable to wear and allows a user to sleep in any position desirable, including supine, lateral or prone.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

FIG. 4 shows a cross section view of a typical anatomy wherein a user's air way is restricted and oxygen cannot easily pass through.

DETAILED DESCRIPTION OF THE INVENTION

Figure 1:
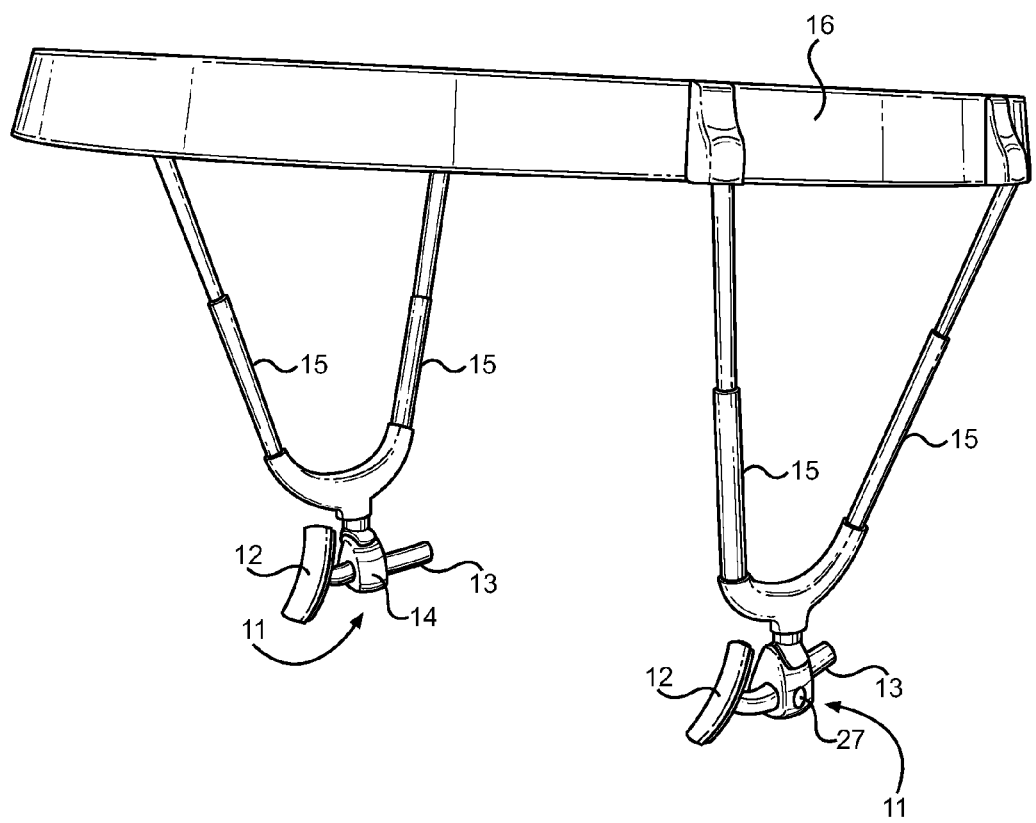
FIG. 1 shows a frontal perspective view of the extra-oral jaw thrust appliance of the present invention.

Reference is made herein to the attached drawings. Like reference numerals are used throughout the drawings to depict like or similar elements of the extra-oral jaw thrust appliance. For the purposes of presenting a brief and clear description of the present invention, the preferred embodiment will be discussed as used for opening and maintaining an airway using an external headgear device that thrusts the mandible forward. The figures are intended for representative purposes only and should not be considered to be limiting in any respect.

Referring now to FIG. 1, there is shown a frontal perspective view of the extra-oral jaw thrust appliance of the present invention. The device comprises an adjustable head band 16 that encircles a user's head above their ears. Attached to the head band 16 and surrounding both ears are a plurality of supports arms 15 that form U-shapes on either side of the user's head that originate from the head band 16 above the ear to and wrap around the underside of each ear, attaching in a first and second position along the head band. Attached to the base of the U-shape support arms 15 are a first and second jaw thruster 11. The jaw thrusters 11 comprise an adjustable mandible thruster pad 12 adapted to abut against the angle of the mandible and displace its natural position for the purposes of forcing the mandible forward to prevent airway restrictions. The pads 12 can be adjusted in a fore-aft direction to create a greater or lesser amount of mandible displacement, depending on user geometry and comfort.

In a particular embodiment, the jaw thruster comprises a pad 12 having a post 13 that slides along an adjustment sleeve 14 and lockable via a set screw 27 or similar securement structure. The pad 12 position is controlled by first adjusting the position of the post 13 within the sleeve 14, and then further adjusting the position of the thruster 11 by changing the length of each support arm 15. The support arm 15 length can be adjusted and locked into a static configuration to provide adequate structure for which to displace the mandible forward. Overall, the device acts as an external head gear without restricting the movement of the user's head or neck, or limiting the sleeping position of the user. It is desired to increase compliance with regard to head gear use by providing a comfortable device that provides minimal interference with the user's natural sleeping position or posture.

Embodiments of the present device include any means to support the thrusters 11 in a position that provides connection to the mandible angle 25 to displace the mandible forward. This includes a head band supporting U-shape supports, supports that form around the backside of the user's ears in a similar fashion as eyeglasses, and finally a head band device that does fully encircles the head, but rather pulls traction against the user's forehead and supports the thrusters behind the mandible 26 angle 25. The displacement of the mandible creates an under bite that prevents the tongue from falling back into the posterior portion of their oropharynx.

Figure 2:
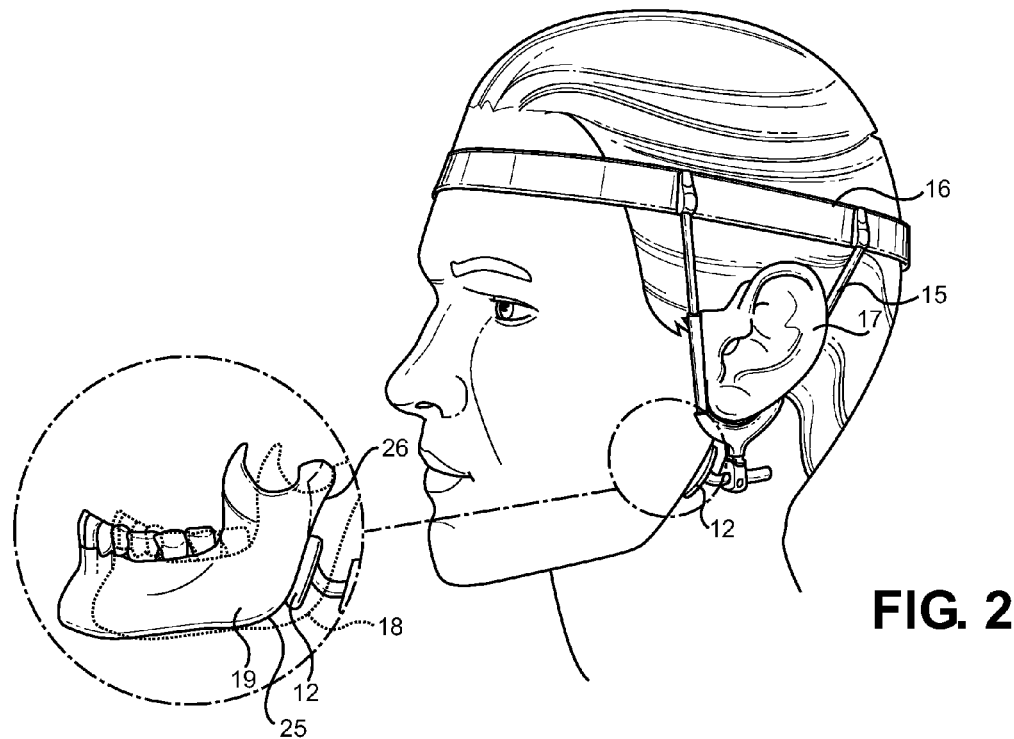
FIG. 2 shows a side perspective view of the present invention in a working position on a user's head, forcing the mandible forward and performing a jaw thrust maneuver.

Referring now to FIG. 2, there is shown a side perspective view of the extra-oral jaw thrust appliance of the present invention in a working position, secured to a user's head via a head band 16 and forcing the user's mandible from a first, natural position 18 to a second, forward position 19. The device is secured to a user's head using a head band securement means 16, wherein a pair of jaw thrusters is positioned below the user's ears 17 and behind the angle of the mandible. The jaw pad 12 of the thruster places load on the mandible and displaces it into a forward position 19 while the pad is supported by a plurality of supports 15 that maintain the thrusters in a static position while in operation.

Figure 3:
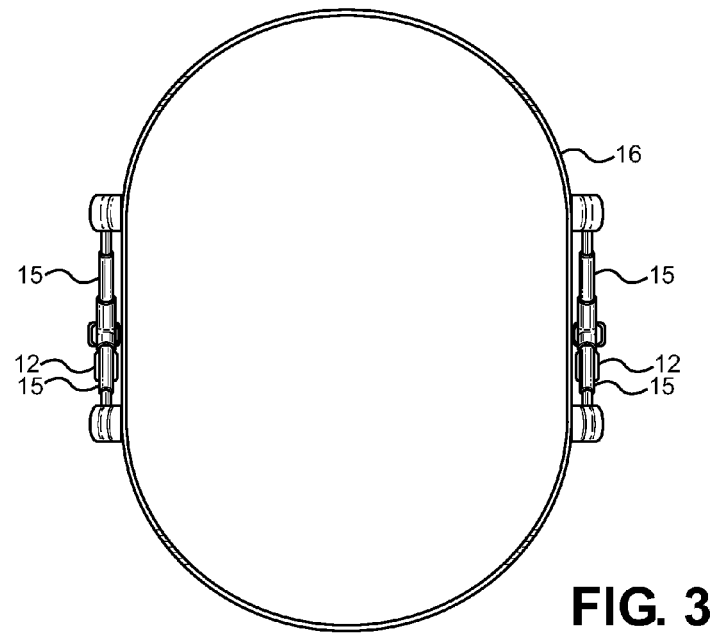
FIG. 3 shows an overhead view of the extra-oral jaw thrust appliance of the present invention.

Referring now to FIG. 3, there is shown an overhead view of the present jaw thrust appliance of the present invention. In an exemplary embodiment, the jaw thrust pads 12 of the present invention are supported by a pair of U-shape supports that connect to a circumferential head band 16 that encircles the user's head. The head band adjustably attaches to the user's head and supports the pads behind the mandible 26 while in a working position, forcing the jaw forward to prevent the tongue and soft tissue of the mouth to restrict air flow into the trachea and lungs. Maintaining this airway is of particular concern during both medical procedures and for those with sleeping disorders, such as excessive snoring and sleep apnea.

For surgeries and medical procedures that are performed under sedation anesthesia, a patient is given enough anesthetics to maintain spontaneous breathing but be unaware of the situation or surroundings. All too often, patients may obstruct their airway, generally by having the tongue fall back into the posterior oropharynx, which requires assistance by the anesthesiologist or nurse anesthetist to maintain airway patency. The second intended situation in which the present invention is well adapted applies to individuals sleeping at night who may voluntarily administer sleeping disorder remedies. Those individuals who snore at night or have problems with sleep apnea can benefit by wearing the disclosed extra-oral appliance to comfortably and effectively prevent collapsing of the user's airway, which is the cause of such disorders. It can be worn while sleeping to provide the same benefit as one under anesthesia—for maintaining a patent airway. This patency is provided in a "hands-free" manner, wherein the airway is maintained by pushing on the angle of the mandible to displace it forward, thereby moving the tongue forward with it and relieving the airway obstruction. The elements of the invention are provided to allow the device to be used in many patient positions (i.e. supine, lateral and prone) with minimal to no interference therewith. This increases compliance and therefore increases the device's effectiveness as a remedy for such disorders or situations in which airway clearance must be diligently monitored.

Figure 4:
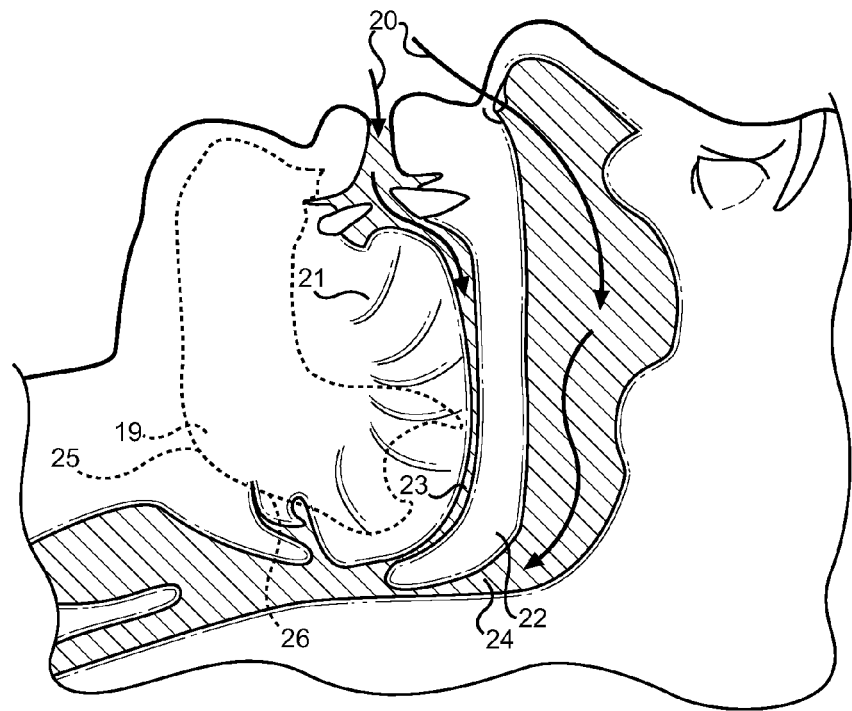
Figure 5:
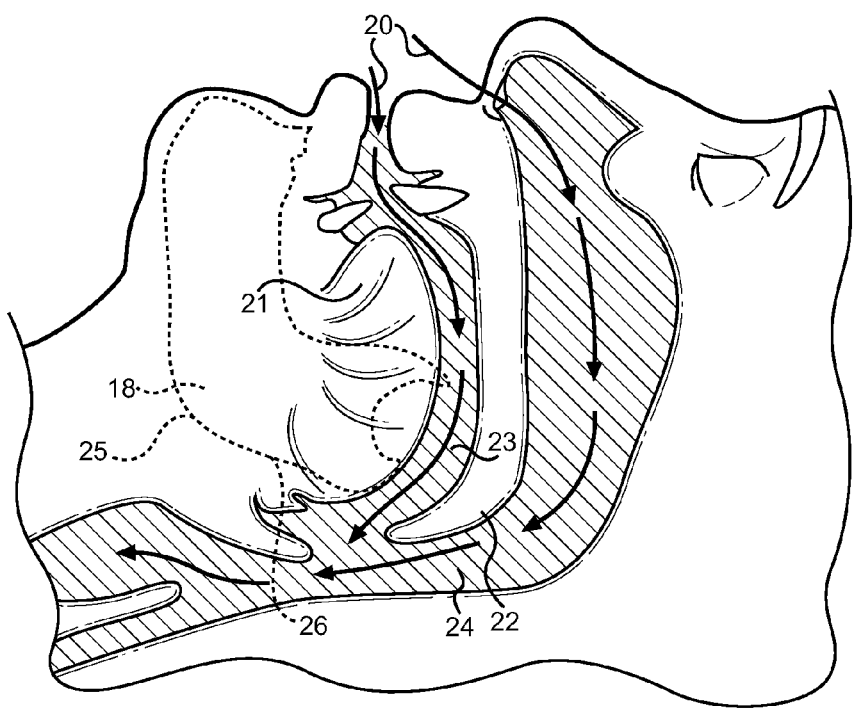
FIG. 5 shows a cross section view of an anatomy of a user wearing the present jaw thrust appliance, wherein the mandible is thrust forward to open the user's airway.

Referring now to FIG. 4 and FIG. 5, there are shown a two cross section views of a user's mouth while breathing. In FIG. 4, the natural state of a user having a restricted airway is shown. The jaw 19 is in a relaxed state, wherein the tongue 21 and soft tissue of the mouth is permitted to collapse the posterior oropharynx 23 airway while the nasopharynx 24 and palate 22 are similarly collapsed, limiting natural breathing and causing a potentially dangerous condition that limits intake 20 of air into the lungs. Shown in FIG. 5 is a cross section view of a user wearing the disclosed extra-oral jaw thrust appliance, wherein the mandible is forced into a forward position 18. In this position, the tongue 21 is prevented from collapsing or occluding the oropharynx 23. Normal, unobstructed breathing is permitted in this position, as the elements of the mouth are prevented from falling into a position that can restrict air flow when in a relaxed state, while under anesthesia or while sleeping naturally.

Overall, the present invention provides a new and improved means of maintaining an open airway and treating sleeping disorders such as excessive snoring and sleep apnea. It is desired to disclose a pair of jaw thruster devices that displace the mandible forward via forward depression of the mandible angle. The thrusters are supported by an external, extra-oral head appliance that encircles the user's head and surrounds the user's ears. Load is transferred from the mandible, in its forward position as it attempts to return to its natural, relaxed position, to the jaw thruster pad and to the thruster support, which is connected to the head gear supported around the user's head. The size, fit and comfort of the device can be adjusted in each element, including the head band diameter, thruster support lengths and fore-aft thruster pad positioning.

It is submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. An extra-oral jaw thrust appliance, comprising:
    a first and second jaw thruster adapted to be positioned behind a user's mandible angle for displacement forward;
    each of said first and second jaw thruster adapted to be positioned under a user's ears;
    each of said first and second jaw thruster attached to a jaw thruster support that surrounds a front portion, a back portion, and a lower portion of said user's ears;
    said jaw thruster support connected to a head gear adapted to be worn on a user's head.

2. The device of claim 1, wherein each of said first and second jaw thruster further comprises an adjustable jaw thruster pad for placement against said user's mandible angle.

3. The device of claim 2, further comprising a post connected to said thruster pad that slides along an adjustment sleeve.

4. The device of claim 2, wherein said jaw thruster pad is adjusted by positioning a post to an adjustment sleeve via a set screw.

5. The device of claim 1, wherein said head gear further comprises:
    a first and second jaw thruster support forming a U-shape that surrounds said user's ears;
    each of said first and second jaw thruster support attached to a head band device that encircles said user's head.

6. The device of claim 5, wherein each of said first and second jaw thruster support and said head band device are adjustable in length to accommodate different users.

7. The device of claim 1, wherein said head gear further comprises:
    a first and second jaw thruster support forming an arc shape that is positioned around the a backside of said user's ears to a front side of said user's ears;
    each of said first and second jaw thruster support attached to a head band device that encircles said user's head.

8. The device of claim 7, wherein each of said first and second jaw thruster support and said head band device are adjustable in length to accommodate different users.

9. An extra-oral jaw thrust appliance, comprising:
    a head gear adapted to be worn on a user's head;
    a first and second jaw thruster supported below said head gear;
    each of said first and second jaw thruster adapted to be positioned behind a user's first and second mandible angle for displacement thereof in a forward direction;
    each of said first and second jaw thruster connected to a jaw thruster support that is adapted to extend from a front portion to a back portion of a user's ears.

10. The device of claim 9, wherein said head gear further comprises:
    a head band device adapted to encircle said user's head;
    a first and second jaw thruster support extending downward from said head band device and forming a U-shape that surrounds said user's ears;
    said first and second jaw thruster support positioning said first and second jaw thruster behind said user's first and second mandible angle.

11. The device of claim 9, wherein said first and second jaw thruster further comprise an adjustable jaw thruster pad adapted to be positioned behind said user's first and second mandible angle.

12. The device of claim 9, wherein each of said first and second jaw thruster support and said head band device are adjustable in length to accommodate different users.

13. The device of claim 9, wherein:
    a head band device adapted to encircle said user's head;
    a first and second jaw thruster support extending downward from said head band device and forming a U-shape that surrounds said user's ears;
    said first and second jaw thruster support positioning said first and second jaw thruster behind said user's first and second mandible angle;
    each of said first and second jaw thruster further comprising an adjustable jaw thruster pad comprising a post connected to said thruster pad adapted to slide along an adjustment sleeve via a set screw, said adjustment sleeve disposed along each of said first and second jaw thrust support.

* * * * *